United States Patent [19]

Dannels

[11] Patent Number: 4,691,065

[45] Date of Patent: Sep. 1, 1987

[54] CHLOROTRIFLUOROETHYLENE TELOMERIZATION PROCESS

[75] Inventor: Bobby F. Dannels, Grand Island, N.Y.

[73] Assignee: Occidental Chemical Corporation, Niagara Falls, N.Y.

[21] Appl. No.: 548,111

[22] Filed: Nov. 2, 1983

[51] Int. Cl.$^4$ .............................................. C07C 17/26
[52] U.S. Cl. ...................................................... 570/139
[58] Field of Search ........................................ 570/139

[56] References Cited

U.S. PATENT DOCUMENTS

| | | | |
|---|---|---|---|
| 2,766,299 | 10/1956 | Schaff | 570/138 |
| 3,651,019 | 3/1972 | Asscher et al. | 570/257 |
| 3,843,734 | 10/1974 | Trebillon | 570/139 |

FOREIGN PATENT DOCUMENTS

| | | | |
|---|---|---|---|
| 715614 | 8/1965 | Canada | 570/257 |
| 20692 | 5/1963 | Japan | 570/257 |
| 340812 | 10/1959 | Switzerland | 570/257 |

*Primary Examiner*—Donald B. Moyer
*Assistant Examiner*—Joseph A. Boska
*Attorney, Agent, or Firm*—James F. Tao; William G. Gosz

[57] ABSTRACT

An improved process for preparaing telomers of chlorotrifluoroethylene comprises the solution telomerization reaction of chlorotrifluoroethylene with carbon tetrachloride in the presence of a catalytic amount of cupric chloride ($CuCl_2$) and an iron reductant. Preferably, the solvent for the system comprises acetonitrile, and the telomerization is carried out under elevated pressure conditions and at a temperature in the range of from about 90° C. to about 150° C. The crude telomer prepared by this process can be fluorinated to produce a stabilized oil or grease.

11 Claims, No Drawings

CHLOROTRIFLUOROETHYLENE TELOMERIZATION PROCESS

BACKGROUND OF THE INVENTION

The present invention relates to an improved process for preparing telomers of chlorotrifluoroethylene, hereinafter designated as "CTFE". CTFE telomers are saturated low molecular weight polymers, typically of general formula $CCl_3(CF_2CClF)_nCl$, where n, the molecular number (the number of repeating units in the telomer chain) is in the range of 1 to 20. Fluorination of the telomer results in replacement of one or more chlorine atoms in the terminal group(s) with fluorine and gives products which are inherently nonflammable, thermally stable, and are particularly suitable for use as hydraulic fluids and high temperature lubricants. Such fluorination can be achieved using a variety of fluorinating agents. For example, British Pat. Nos. 712,184 and 761,053 disclose the fluorination of CTFE oils using both chlorine trifluoride and cobalt trifluoride. The use of hydrofluoric acid as a fluorinating agent for CTFE oils is also disclosed in U.S. Pat. No. 2,636,908, while U.S. Pat. No. 2,886,607 illustrates the use of antimony trifluoride and antimony pentachloride as fluorinating agents.

Various methods of preparing CTFE telomers are known in the prior art and have been practiced commercially for many years. An article by William T. Miller, Jr. et al in *Industrial and Engineering Chemistry*, pages 333–337 (1947), entitled "Low Polymers of Chlorotrifluoroethylene", describes a process for producing low molecular weight polymers of CTFE by carrying out the polymerization in a solution of chloroform using benzoyl peroxide as a polymerization promoter. Other solvents disclosed in the reference as being useful for this purpose include carbon tetrachloride and tetrachloroethylene. The solution is heated in a pressure vessel for 1¾ hours at 100° C. and the unreacted CTFE monomer and chloroform are removed by distillation, leaving a "crude" telomer of the general formula $CHCl_2(CF_2CClF)_nCl$, which can be further heated and distilled to yield products ranging from a light oil to a semi-solid wax or grease.

U.S. Pat. No. 2,793,201, issued May 21, 1957, discloses improved promoters for polymerizing CTFE monomers to produce low molecular weight polymers. Specific promoters disclosed in the reference include various peroxides such as bis-(trichloroacetyl) peroxide and bis-(perchloroacrylyl) peroxide. The use of such promoters produces a more stable polymer by eliminating the amount of reactive hydrogen present in the polymer.

Another process which has been developed for producing low molecular weight CTFE polymers is described in U.S. Pat. No. 2,788,375, issued Apr. 9, 1957. This process comprises reacting CTFE with a saturated organic bromo compound, such as bromotrichloromethane, in the presence of actinic light in a deoxygenated system to obtain saturated bromopolychlorofluoro compounds containing one or more CTFE units per molecule. These saturated bromopolychlorofluoro compounds can then be converted to corresponding polychlorofluoro compounds by treatment with chlorine, and subsequently fluorinated using, for example, cobalt trifluoride or chlorine trifluoride, in combination with antimony catalysts, to yield more highly fluorinated products.

A more recent development in this field is described in a series of articles by Y. Pietrasanta et al entitled "Telomerization by Redox Catalysis" appearing in the *European Polymer Journal*, Vol. 12 (1976). This technology involves the reaction of a chlorinated telogen, such as carbon tetrachloride, with CTFE in the presence of benzoin and a suitable redox catalyst, such as ferric chloride hexahydrate ($FeCl_3 \cdot 6H_2O$). The telomerization reaction is suitably carried out in acetonitrile which is a common solvent for the reactants and catalysts. The telomerization reaction can be illustrated as follows:

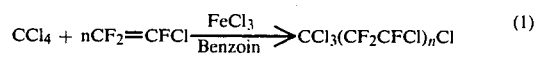

$$CCl_4 + nCF_2=CFCl \xrightarrow[\text{Benzoin}]{FeCl_3} CCl_3(CF_2CFCl)_nCl \quad (1)$$

The redox method has the advantage of directly preparing a high yield of low molecular weight product without the necessity of cracking or fractionating a higher molecular weight polymer.

It is known that benzoin acts as a reducing agent for $Fe^{+3}$ ions in solution and that, in the absence of benzoin, product yield falls to less than 5%. See *European Polymer Journal*, supra. However, there are certain disadvantages associated with the use of benzoin in the redox telomerization process which could effectively render uneconomical any commercial scale process based on this technology. For example, benzoin must be removed from the crude telomer prior to fluorination or the fluorinated product will contain unsaturation as determined by the $KMnO_4$ test and, as a result, will not meet product specifications. Removal of the benzoin from the crude telomer requires the use of an absorption column, such as a column of activated alumina, which not only removes benzoin but retains a significant amount of telomer which must be reclaimed using, for example, solvent extraction. The use of an activated alumina column is a costly and time-consuming procedure.

It has also been proposed to substitute nickel or some equivalent metal reductant for benzoin in reaction (1). See, in this regard, commonly assigned copending application Ser. No. 374,561, filed May 3, 1982. This has the advantage of simplifying the reaction by eliminating the necessity for removing benzoin from the reaction mixture, which is a time-consuming and costly operation. In addition, when telomers prepared using such a substituted system are directly fluorinated, the resulting product will not contain unsatisfactory levels of unsaturation. However, the substitution of nickel for benzoin produces a telomer distribution having an increased proportion of higher molecular weight telomers. This is unfortunate since the higher weight telomers are less useful commercially than the lighter telomers. Consequently, it is desirable to reduce the higher weight fraction to more acceptable levels.

It is therefore a principal object of the present invention to provide an improved process for preparing CTFE telomers with enhanced levels of lower molecular weight material. It is a further object of this invention to provide a process for preparing CTFE telomers which can be directly fluorinated after removal of solvent and unreacted materials without containing unacceptable levels of unsaturation.

SUMMARY OF THE INVENTION

In accordance with the present invention, there is provided an improved process for preparing telomers of chlorotrifluoroethylene comprising reacting chlorotrifluoroethylene with carbon tetrachloride in the presence of a catalytic amount of $CuCl_2$ and an iron reductant. The reaction is conducted in a solvent which preferably comprises acetonitrile. The telomerization reaction is preferably conducted at a pressure in the range of from about 150 p.s.i. to about 300 p.s.i. and a temperature in the range of from about 90° C. to about 150° C.

The crude telomers prepared by this process can be fluorinated directly after removal of solvent and unreacted materials using conventional fluorination techniques. The product is a stabilized material which has fluorine-substituted end groups, reduced levels of higher molecular weight telomers, and acceptable levels of product saturation.

DESCRIPTION OF THE PREFERRED EMBODIMENTS

The telemerization process of the present invention provides for the reaction of chlorotrifluoroethylene with carbon tetrachloride in a solvent, such as acetonitrile, in the presence of a catlytic amount of $CuCl_2$ and iron and can be illustrated as follows:

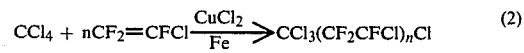

$$CCl_4 + nCF_2=CFCl \xrightarrow[Fe]{CuCl_2} CCl_3(CF_2CFCl)_nCl \quad (2)$$

The molecular weight distribution of the telomer is dependent on several factors, including the relative concentration of $Cu^{+2}$ ions in the solution, the rate of reduction of $Cu^{+2}$ ions to $Cu^{+1}$ ions, and the relative concentration of the reactants in the solution. By carefully controlling these conditions during the telomerzation reaction, it is possible to produce a telomer having a relatively precise molecular weight distribution in the desired range, i.e. corresponding to a molecular number of from about 1 to about 20.

It has been found necessary to introduce an iron reductant into the reaction mixture to reduce the $Cu^{+2}$ ions at a moderate rate. The use of benzoin as a reducing agent, although effective, has the disadvantage of requiring an additional unit operation, i.e. adsorption using, for instance, a column of activated alumina, for removal of the benzoin prior to fluorination. The iron reductant may be physically present in the reaction mixture in a variety of forms, such as a powder, particles of various sizes, wires, plates, or as a cladding material on the internal surface of the reactor vessel. The preferred form is a finely divided powder which is uniformly dispersed in the reaction vessel by means of mechanical agitation, such as in a stirred reactor. The iron reductant is preferably present in the reaction mixture in the range of from about 0.05% to about 5% by weight of CTFE. It is also desirable to maintain the concentration of $CuCl_2$ in the range of from about 0.05% to about 5% by weight of CTFE.

The telomerization reaction is preferably conducted in a stirred reactor under elevated temperature and pressure conditions, with temperatures generally ranging from about 90° C. to about 150° C., and pressures generally in the range of from about 50 p.s.i. to about 400 p.s.i.

The crude CTFE telomer which is prepared according to the procedure described above, can then be stripped of solvent and unreacted monomer and fluorinated directly with a suitable fluorinating agent to produce stabilized telomers. Fluorinating agents which can be employed for this purpose include cobalt trifluoride and chlorine trifluoride, among others.

The following examples are intended to further illustrate the various embodiments and advantages of the present invention without limiting it thereby. Example 1 illustrates the preparation of crude CTFE telomers according to the process of the present invention. Examples 2 and 3 are comparative examples illustrating the preparation of crude CTFE telomers using nickel/$FeCl_3$ and benzoin/$FeCl_3$ systems, respectively.

EXAMPLE 1

A 600 ml. Parr Ti glass-lined autoclave was charged with a solution of 0.007 moles of $CuCl_2$ dissolved in 1.46 moles of acetonitrile. 0.59 Moles of $CCl_4$ was added to the autoclave. 0.04 Moles of Fe was added, and the autoclave was then closed and pressurized with $N_2$ to 200 psig to check for leaks. The $N_2$ was bled out and 0.96 moles of CTFE was added from a small cylinder. After heating to 125° C. a pressure of 280 psig was recorded. When the pressure began to drop, 0.29 moles of CTFE was introduced from a small cylinder in a water bath having a temperature sufficient to give a pressure approximately equal to the maxiumu pressure upon heating the autoclave. This pressure was maintained for about 4 hours.

The crude product was first washed with 10% HCl and then with water until the wash was essentially neutral. This product was then stripped to yield 100 grams of material. Gas chromatographic analysis of this material revealed the following distribution of telomers:

| $CCl_3(CF_2CFCl)_nCl$ Telomer Species | |
|---|---|
| n Value | Amount % |
| 1 | 27.2 |
| 2 | 18.7 |
| 3 | 13.1 |
| 4 | 8.5 |
| 5 | 5.8 |
| 6 | 4.0 |
| 7 | 2.6 |
| 8 | 1.5 |
| 9 | 0.8 |
| 10 | 0 |
| 11 | 0 |
| 12 | 0 |
| >12 | 8.8 |
| Impurities | 7.6 |

EXAMPLE 2

A 600 ml. Parr Ti Glass-lined autoclave was charged with a solution of 0.009 moles of $FeCl_3$ dissolved in 1.1 moles of acetonitrile. 1.2 moles of $CCl_4$ was added to the autoclave. 0.026 moles of nickel was added, and the autoclave was then closed and pressurized with $N_2$ to 200 psig to check for leaks. The $N_2$ was bled out and 0.96 moles of CTFE was added from a small cylinder. After heating to 115° C. a pressure of 250 psig was recorded. When the pressure began to drop, 1.0 moles of CTFE was introduced from a small cylinder in a water bath having a temperature sufficient to give a pressure approximately equal to the maximum pressure reached upon heating the autoclave. This pressure was maintained for about 4 hours.

The crude product was first washed with 10% HCl and then with water until the wash was essentially neutral. This product was then stripped to yield 110 grams of material. Gas chromotography analysis of this material revealed the following distribution of telomers:

| $CCl_3(CF_2CFCl)_nCl$ Telomer Species | |
|---|---|
| n Value | Amount % |
| 1 | 24.2 |
| 2 | 16.2 |
| 3 | 12.5 |
| 4 | 9.0 |
| 5 | 7.5 |
| 6 | 5.0 |
| 7 | 3.8 |
| 8 | 2.3 |
| 9 | 0.9 |
| 10 | 0 |
| 11 | 0 |
| 12 | 0 |
| >12 | 14.8 |
| Impurities | 3.5 |

EXAMPLE 3

A 600 ml. Parr Ti glass-lined autoclave was charged with a solution of 0.009 moles of $FeCl_3$ dissolved in 1.54 moles of acetonitrile. 0.71 moles of $CCl_4$ was added to the autoclave. 0.014 moles of benzoin was added, and the autoclave was then closed and pressurized with $N_2$ to 200 psig to check for leaks. The $N_2$ was bled out and 1.12 moles of CTFE was added from a small cylinder. After heating to 115° C. a pressure of 290 psig was recorded. When the pressure began to drop, 0.96 moles of CTFE was introduced from a small cylinder in a water bath having a temperature sufficient to give a pressure approximately equal to the maximum pressure reached upon heating the autoclave. This pressure was maintained for about 4 hours.

The crude product was first washed with 10% HCl and then with water until the wash was essentially neutral. This product was then stripped to yield 106 grams of material. Gas chromatographic analysis of this material revealed the following distribution of telomers:

| $CCl_3(CF_2CFCl)_nCl$ Telomer Species | |
|---|---|
| n Value | Amount (%) |
| 1 | 22.6 |
| 2 | 16.3 |
| 3 | 15.0 |
| 4 | 12.2 |
| 5 | 8.0 |
| 6 | 5.9 |
| 7 | 4.1 |
| 8 | 3.4 |
| 9 | 2.3 |
| 10 | 1.1 |
| 11 | 0 |
| 12 | 0 |
| >12 | 3.0 |
| Impurities | 6.0 |

While various embodiments and exemplifications of this invention have been shown and described in the specification, modifications and variations thereof will be readily appreciated by those skilled in the art. It is to be understood, therefore, that the appended claims are intended to cover all such modifications and variations which are considered to be within the scope and spirit of the present invention.

What is claimed is:

1. A process for preparing a distribution of telomers of chlorotrifluoroethylene of general formula $CCl_3(CF_2CFCl)_nCl$, where n is from about 1 to about 20, consisting essentially of reacting chlorotrifluoroethylene with carbon tetrachloride in the presence of a catalytic amount of $CuCl_2$ and iron, said reaction being conducted in a solvent at a temperature of from about 90° C. to about 150° C.

2. The process of claim 1 wherein the solvent is acetonitrile.

3. The process of claim 2 wherein the $CuCl_2$ is present in the reaction mixture in an amount of from about 0.05% to about 5% by weight of chlorotrifluoroethylene.

4. The process of claim 3 wherein the iron is present in the reaction mixture in an amount of from about 0.05% to about 5% by weight of chlorotrifluoroethylene.

5. The process of claim 2 wherein the telomerization reaction is conducted at a pressure of from about 150 p.s.i. to about 300 p.s.i.

6. A process for preparing stabilized telomers of chlorotrifluoroethylene, consisting essentially of the steps of:
   (a) reacting chlorotrifluoroethylene with carbon tetrachloride in the presence of a catalytic amount of $CuCl_2$ and iron to prepare a distribution of telomers of general formula $CCl_3(CF_2CFCl)_nCl$, where n is from about 1 to about 20, said reaction being conducted in a solution of acetonitrile at a temperature of from about 90° C. to about 150° C.,
   (b) removing solvent and unreacted materials from the telomers produced in step (a), and
   (c) directly fluorinating the telomers from step (b) to stabilize the telomers.

7. The process of claim 6 wherein the $CuCl_2$ is present in an amount of from about 0.05% to about 5% by weight of chlorotrifluoroethylene.

8. The process of claim 7 wherein the iron is present in an amount of from about 0.05% to about 5% by weight of chlorotrifluoroethylene.

9. The process of claim 6 wherein the solvent and unreacted materials are removed from the telomers by evaporation.

10. The process of claim 6 wherein the telomers are fluorinated with chlorine trifluoride.

11. The process of claim 6 wherein the fluorination reaction in step c) is conducted at a temperature of from about 120° C. to about 200° C.

* * * * *